United States Patent [19]

Hirsch

[11] Patent Number: 5,885,614

[45] Date of Patent: Mar. 23, 1999

[54] USE OF ODORANTS TO TREAT MALE IMPOTENCE, AND ARTICLE OF MANUFACTURE THEREFOR

[76] Inventor: Alan R. Hirsch, 180 E. Pearson #4702, Chicago, Ill. 60611

[21] Appl. No.: 606,544

[22] Filed: Feb. 23, 1996

[51] Int. Cl.$^6$ ....................................................... A61K 9/48
[52] U.S. Cl. .......................... 424/451; 424/451; 424/489; 424/434
[58] Field of Search ..................................... 424/451, 489, 424/58, 45, 46, 434

[56] References Cited

PUBLICATIONS

P.D. MacLean, "Cerebral evolution of emotion," in Lewis and Haviland (eds.), *Handbook of Emotions*, p. 77, The Guilford Press, New York, NY (1993).
H. Sugano, *JASTS* 12:8 (Abstract)(1988).
J. Borden, "This story stinks, but it might be quite lucrative," *Chicago Business Crain's*, Metro Chicago's Business Authority (Dec. 2–8, 1991).
A. R. Hirsch, *Advances in Consumer Research* 19: 390–395 (1992).
J. R. King, "Anxiety Reduction Using Fragrances," in *Perfumery, The Psychology and Biology of Fragrance*, pp. 147–165, Van Toller & Dodd (eds.), Chapman and Hall, Ltd., London (1988)).
Erlichman, H. and Bastone, L., "Olfaction and Emotion", *Science of Olfaction*, pp. 410–417, Serby and Choboro (Eds.), Springer–Verlag, New York, NY (1992).
Erlichman, H. and Bastone, L., *Perfumer & Flavorist* 16:11–12 (1991).
Ludvigson & Rottman, *Chemical Senses* 14:525–536 (1989).
Ehrlichman, H. and Bastone, L., *Perfumer & Flavorist* 16:11–12 (1991).
Baron, R.A., *Journal Applied Social Psychology* 20:368–384 (1990).
Hirsch, A. R. and L.H. Johnston, *Chemical Senses* 19: 46 (Abstr. No. 121)(1994).
Hirsch, A. R. and L.H. Johnston, *ACHEMS–XVI*: Abstract No. 142 (1994).
Hirsch, A. R. and L.H. Johnston, *Chemical Senses* 20(1): 77–78 (1995).
Amoore et al., *Rhinology* 21:49–54 (1983).
R. L. Doty et al., *Ann. Neurol.* 25: 166–171 (1989).
Doty et al., *Chemical Senses* 10:297–300 (1985).
R. Doty, *The Smell Identification Test: Administration Manual* 1983: 13–14, Philadelhia: Sensonics, Inc. (1983).
J.F. Gent, in *Clinical Measurement of Taste and Smell*, pp. 107–116, H.L. Meisolman (eds.), 602pp., MacMillan, Ny (1986).
Hirsch, A.R. and Cain D.R., *Chemical Senses* 17:642–643 (1992).
E. Koss et al., *Neurology* 38: 1228–1232 (1988).
A.R. Hirsch, *The Nose Knows*, Chicago Medicine, pp. 28–31, (Jul. 21, 1990).
A.R. Hirsch and J.J. Kim, *Phychosomatic Medicine*, 57:83 (1995).

*Primary Examiner*—Thurman K. Page
*Assistant Examiner*—William E. Benston, Jr.
*Attorney, Agent, or Firm*—Godfrey & Kahn, S.C.

[57] ABSTRACT

A method is provided for inducing or enhancing penile erection through the delivery of odorants for inhalation. The administration of odorants provides an increase in blood flow to the penis, and a therapeutic aid to stimulate sexual activity and alleviate male vasculogenic impotence.

23 Claims, No Drawings

USE OF ODORANTS TO TREAT MALE IMPOTENCE, AND ARTICLE OF MANUFACTURE THEREFOR

BACKGROUND OF THE INVENTION

In men, the genital component of the excitement phase of the sexual response cycle is manifested by penile erection and scrotal elevation (Kolodny, Masters and Johnson, *Textbook of Sexual Medicine*, pages 507–508, Little, Brown and Company, Boston, Mass. (1979)). Erection is basically a cardiovascular event that is controlled by the nervous system. The first physical sign of sexual excitation is a change in penile blood flow. Blood flow increases to the penis with sexual excitement and is reduced with sexual inhibition.

Male erectile dysfunction, or impotence, is the inability to achieve or sustain an erection of sufficient rigidity to have sexual intercourse. The causes of impotence are psychological and/or organic (i.e., endocrinologic, neurogenic and vasculogenic). Ten to fifteen percent of male impotence is organic in nature. Organic causes can be from local lesions of the genitalia, endocrine diseases, organic lesions of the nervous system, and/or vasculogenic impotence from reduced blood flow is the most common organic cause usually seen in diabetes. Impotence may be a side effect of a therapeutic drug or associated with a disease such as multiple sclerosis, diabetes and sickle cell anemia, and can be exacerbated by smoking, inadequate diet among other factors. Emotional disturbances, including stress, fatigue or distraction, can also cause impotence.

In the sexual response, neuromuscular events simultaneously increase the amount of blood entering the organ and decrease the rate at which blood is allowed to leave it. Three vascular changes have been indicated in causing erection: shunting of blood into the cavernous spaces, contraction of muscular polsters on deep efferent veins, and vasoconstriction-induced reduction in superficial penile blood flow (G. Conti, *Octa. Anat.* 14:17 (1952)). As a function of the autonomic nervous system, penile engorgement is controlled by arterial flow through the pudendal artery and the smaller arteries to the penis. The increased arterial flow is accomplished by active dilatation of the arterioles. The process is reversed by the sudden constriction of the arterioles that accompanies ejaculation.

Alteration of blood flow to and from the penis is considered to be the most frequent organic cause of impotence. Vasculogenic impotence results from either arterial occlusion, i.e., the obstruction of adequate blood flow to the penile arteries, or excess venal outflow (cavernovenous leaking).

Treatment of impotence can include counseling directed toward dealing with the male's insecurities and feelings to reduce fears of sexual performance. Treatments for male impotence include surgery, penile prostheses implants including flexible rods and inflatable balloons, drugs such as vasodilators given to induce an erection as an ointment for topical application or a solution for transurethral injection, and external aids such as penile splints to support the penis or constricting rings to alter the blood flow through the penis. A drawback of those systems is their invasiveness, unwanted side effects, cost, inconvenience, and complexity.

Accordingly, an object of the invention is to provide a method of stimulating the male sexual response and inducing penile erection, that is non-invasive and easy to perform. Another object is to induce normal male sexual arousal.

SUMMARY OF THE INVENTION

These and other objects are achieved by the present invention which is directed to a method for stimulating the male sexual response through the delivery of an odorant substance for inhalation. The use of the odorants is particularly useful as adjuvants for inducing or enhancing an erection, and as aids for a non-invasive treatment of male vasculogenic impotence.

It was found that the administration of odorants for inhalation by a male individual having a normal olfactory ability effectively increased penile blood flow from about 2–40%, and enhanced sexual arousal. Preferred odorants are those that provided a 20–40% increase in blood flow to the penis, which includes lavender, oriental spice, cola and orange, and odorant mixtures of lavender and pumpkin pie, doughnut and black licorice, and pumpkin pie and doughnut. The odorants are useful as adjuvants to augment penile blood flow and as aids in the treatment of male impotence, and to enhance sexual arousal in normal males, i.e., those without sexual dysfunction.

DETAILED DESCRIPTION OF THE INVENTION

The present invention provides a non-invasive method of increasing blood flow to the penis to augment penile erection, and of treating vasculogenic impotence through the use of odorants. The method is particularly useful for males who have a normal olfactory ability. Administration of the odorant to a male subject will increase penile blood flow such that in a normosmic person for which the odor is hedonically positive, the blood flow will increase by about 2–40% compared to blood flow without being given the odorant. Preferably, the odorant induces or enhances an erection sufficient for vaginal penetration.

Preferably, an odorant is administered that will increase penile blood flow by about 2–60%, preferably about 15–50%. Preferred odorants are those that increase blood flow by about 20–40%, which include, for example, lavender, oriental spice, cola and orange odorants, and odorant mixtures such as lavender and pumpkin pie, doughnut and black licorice, pumpkin pie and doughnut, and lavender and doughnut. Odorants useful in the present method are commercially available, for example, from International Flavors and Fragrances, Inc. (IFF), New York, N.Y.

The precise magnitude of a loss of smell may be determined by means of an odor threshold test. According to that test, an odorant substance such as butyl alcohol, phenyl ethyl alcohol or pyridine, is combined in an odorless liquid medium to provide a series of dilutions, or binary steps, of the odorant. For each successive binary step up the dilution scale, the odorant is present, for example, at one half the concentration of the preceding step. The highest concentration of the odorant usually provides the substance at an irritant level. The patient is presented with the series of dilutions in ascending order, and is asked to compare each dilution step to at least one control stimulus, such as odorless propylene glycol.

A "normosmic" individual is able to detect the odor of an odorant substance without irritant sensations when the substance is presented at a concentration within a range of the average normal threshold for the substance. A "hyposmic" individual is one who has a reduced capacity of the olfactory nerve being able to detect an odorant substance by its odor at a concentration, or decismel level, above that of a normosmic individual yet below its irritant concentration level. An "anosmic" individual is one who has essentially no olfactory nerve capacity being unable to detect the odor of the odorant substance, but has trigeminal nerve function, being able to detect an odorant substance by means of irritant, tingling sensations when it is present at an irritant concentration. A patient who is able to detect pyridine vapor by means of irritant, tingling sensations caused by stimulation of the trigeminal nerve, but who cannot distinguish a pyridine odor at a lower concentration without such sensation, is considered to be anosmic having no olfactory nerve sensitivity. The term "microsmic" is synonymous with hyposmic.

The only limitation on the character of the odorant that is used is that it must be suprathreshold in intensity and not trigeminal in nature. According to the method of the invention, an odorant and/or odorant mixture is administered to a male subject/patient for sniffing and inhalation into the nasal passageway, to deliver an amount of the odorant effective to increase penile blood flow which is a suprathreshold level but not irritative in nature.

An odorant is presented at a suprathreshold level when the decismel level or concentration of the odorant is high enough to be detected by a normosmic individual. At its irritative level, the odorant level or concentration is so high that the odorant stimulates predominantly the trigeminal nerve rather than the olfactory nerve and, hence, is perceived as noxious. The irritation threshold of the patient is the lowest concentration of the substance that causes immediate stinging or burning sensations in the nose, or stinging or lacrimation of the eye. (See, J. F. Gent, in *Clinical Measurement of Taste and Smell*, pages 107–166, H. L. Meiselman et al. (eds), 602 pp., MacMillan, NY (1986); R. L. Doty et al., *Ann. Neurol.* 25: 166–171 (1989); E. Koss et al., *Neurology* 38: 1228–1232 (1988); R. Doty, *The Smell Identification Test: Administration Manual* 1983: 13–14, Philadelphia: Sensonics, Inc. (1983)).

The effect of the odorant and/or odorant mixture can be assessed objectively by administering a test to the subject to measure initial penile blood flow, and then re-testing the blood flow after being given the odorant. The effectiveness of the odorant on the subject can be observed by comparing the amount of penile blood flow before and after inhaling the odorant.

The use of the odorant or odorant/mixture is useful for increasing penile blood flow in a male individual who does or does not suffer from vasculogenic impotence to improve penile erection. Male vasculogenic impotence is the result of primary small vessel disease or is a secondary symptom of a disease such as diabetes, atherosclerosis or amyloidosis, for example.

The odorant can be delivered to the subject in the form of a liquid solution, aerosol spray, solid, microcapsules, or other suitable form to deliver an amount of the odorant for sniffing by the person to increase blood flow to the penis and effectuate and/or enhance penile erection and sexual arousal. A preferred amount of the odorant that is delivered is a suprathreshold but not irritative level.

The odorant substance can be administered in combination with an odorless liquid carrier such as mineral oil or water, and can be formulated with a viscosity effective to allow for aerosolization. The odorant can be dispensed, for example, by means of a cloth material that is coated with the odorant, as a solid or liquid form contained in a capped vessel, as a spray from an aerosol or pump-type spray device, as a nasal spray, by opening a blister pack or scratch-and-sniff odor patch containing the odorant in the form of microspheres, a vaporous emission from a pen-like dispenser containing a liquid form of the odorant adsorbed to a wicking material, a vapor from a solid or liquid air freshener, a lotion or cream, perfume or cologne, potpourri, incense, a lightbulb ring or candle, and the like. The odorant can be provided in a portable dispenser for ready individual and personal use, for example, by means of a pen-like delivery device, a blister pack, a small vial of lotion, a booklet of scratch-and-sniff odor patches, and the like, that include an effective amount of the desired odorant substance.

The odorant substance or odorant mixture can be packaged as a part of an article of manufacture, or kit, for use in increasing penile blood flow and/or enhancing penile erection. The kit can include in association, for example, an effective amount of an odorant and/or odorant mixture in a non-reactive, biocompatible carrier and/or optional additives as desired such as an antioxidant, preservative, and the like; and means for containing the odorant such as a vial, jar, pouch, can, bottle, cloth, aerosol can, blister pack, scratch-and-sniff odor patch, pen-like device, and the like. The containing means can include means for spraying by aerosolization or pumping. The kit can further include means for instructing the user about the use of the odorant and/or mixture to stimulate penile blood flow, in the form of a label or tag attached to the packaging and/or a printed package insert. The parts of the kit can be contained or separately packaged within a packaging material, such as a box or bag.

The invention will be further described by reference to the following detailed examples, wherein the methodologies are as described below. These examples are not meant to limit the scope of the invention that has been set forth in the foregoing description. Variation within the concepts of the invention are apparent to those skilled in the art. The disclosures of the cited references are incorporated by reference herein.

EXAMPLE

A randomized double-blind study was conducted to assess the effect of odorants on penile blood flow, a measure of the level of male excitation. Thirty-one men underwent penile blood flow measurements with a bi-directional doppler ultrasound while wearing masks with a total of 46 different odors and 2 control masks. All subjects underwent standardized smell tests. The brachial/penile index (BPI) with blank masks (as baseline) was compared with each odorized mask for each individual as well as for the group as a whole. Data was analyzed using the Wilcoxan Rank Sum Test and Spearman's Rank Correlation Coefficients.

The odors with the greatest increase in BPI were a mixture of lavender and pumpkin pie, doughnut and black licorice, and pumpkin pie and doughnut. In subjects with normal olfactory ability and whose partners wear cologne, lavender had the greatest impact on BPI ($p=0.03$). The ability for oriental spice ($p=0.01$), cola ($p=0.02$) and lavender ($p=0.02$) to increase BPI positively correlated with the number of times the subject had intercourse in the last month. The results showed that, in those men with a normal olfactory ability, a variety of odors can increase penile blood flow.

Testing Procedure. Thirty-one male volunteers from 18–64 years of age (mean 30.2) underwent olfactory testing with the University of Pennsylvania Smell Identification Test (UPSIT), a 40-question forced-choice, scratch-and-sniff identification test and the Chicago Smell Test, a 3-item detection and identification test (Doty et al., *Chemical Senses* 10:297–300 (1985); Hirsch et al., *Chemical Senses* 17:642–643 (1992); Hirsch et al., *Chemical Senses* 18 (5):570–571 (1993); Hirsch et al., *Chemical Senses* 18 (5):571 (1993)).

Each male subject was also queried as to sexual preferences, sexual practices, and odor hedonics. Questions asked were as follows: age; marital status (s; m; w; d); height and weight; whether an odor made him recall his childhood and, if yes, what odor; if he wears a cologne and, if yes, what cologne; if he has diabetes; if he had any difficulty with obtaining an erection in the last 30 days and, if yes, the approximate number of times; if he smokes and, if yes, the number of cigarettes daily; favorite food (specific); least favorite food (specific); approximate number of times he had sexual intercourse in the last 30 days; approximate number of sexual partners in the last 30 days; sexual preference (male; female); how satisfied with his current sexual activity on a rating scale of 1-2-3-4-5, where 1=very unsatisfied and 5=satisfied; number of times he had an erection upon awakening within the last 30 days on a scale of 1-2-3-4-5, where 1=never, 3=sometimes, 5=always; and if there was a particular odor to cause him to have an erection within the last 30 days (yes, no) and, if yes, what odor.

Subjects underwent assessment of level of sexual arousal as determined by the brachial penile index (Laws et al., "The Penile Plethysmograph," in A Practioner's Guide to Treating the Incarcerated Male Sex Offender, pages 85–93, B. K. Schwartz and H. R. Cellini (eds.), U.S. Department of Justice, National Institute of Corrections, Washington D.C. (1988)). The test was performed with the FLOSCOPE ULTRA Pneumoplethysmograph following manufacturer's protocol (LifeSigns Corporation, "The PC Compatible FLOSCOPE ULTRA Vascular Lab", Minneapolis, Minn. (1994)). With this instrument, both penile and brachial blood pressures were measured and their ratio calculated, thus controlling for systemic effects. This allowed specific non-invasive assessment of penile blood flow.

All subjects underwent assessments as follows. After being attached to the plethysmograph, 3 minutes were allowed for acclamation to the experimental environment. Following this, a blank control mask was applied for 1 minute and then brachial penile index was recorded. The masks were made of 3-M paper surgical masks, and were designed to cover the nose and mouth. The mask was removed and then the 46 odorized masks were randomly presented in a double-blinded fashion. The odorized masks were prepared by applying about 1 drop of odorant to provide a non-irritant but suprathreshold level of the scent (i.e., a level wherein the subject could detect the odor was present, but was not so high as to be noxious or primarily trigeminal in nature. The odorants are shown in Table 1.

Each mask was worn for 1 minute, and brachial penile index was then recorded. There was then a 3-minute "washout" period between masks which involved breathing filtered air in a relative odor-free environment. At the end of the testing, an additional blank mask was worn for 1 minute, and a brachial penile index recorded. The effects of the odors were assessed by comparing brachial penile index with each individual odor as compared to the average of the control masks.

Statistical Analysis. The statistical analysis was provided by Sally Friels, Ph.D. of the University of Illinois School of Public Health, Chicago, Ill. Statistical significance was defined if a p value was less than or equal to 0.05. Data analysis included the following nonparametric tests: Signed Rank test, Wilcoxan Rank Sum Test, and Spearman's Rank Correlation Coefficient (T. Colton, *Statistics in Medicine*, Little Brown & Co., Boston, Mass. (1974)); E. L. Lehmann, *Nonparametrics: Statistical Methods Based on Ranks*, Holden-Day, New York, N.Y. (1975)).

Demographics. GENERAL: 77.4% (n=24) of the male subjects were single, 16.1% (n=5) were married, and 6% (n=2) were divorced. All subjects lived in Chicago and surrounding suburbs. Subjects were recruited through radio solicitation. All subjects were literate in English.

OLFACTION: In response to the questionnaire, 55% (n=17) of the subjects admitted to olfactory evoked nostalgic experience (A. R. Hirsch, *Advances in Consumer Research* 19:390–395 (1992)). 61% (n=19) did not smoke, 29% (n=9) smoked one ore less than one pack per day, and 10% (n=3) smoked between 1.1 to 2 packs per day. Given age and sex, UPSIT scores were graded based on published normal values (Doty et al., *Chemical Sense* 10:297–300 (1985)). Given these, 51% (n=16) had normal olfactory ability, whereas 48% (n=15) were microsmic or anosmic. 71% (n=22) customarily wore cologne. Of those who currently had regular sexual partners (n=23), 83% (n=19) of their partners customarily wore perfume or cologne.

SEXUAL: 74% (n=23) of the subjects had at least one regular sexual partner. None admitted to erection difficulties in the last 30 days. The frequency of intercourse over the last 30 days varied from zero in 19% (n=6) to 25 in 6% (n=2) described as having more than one sexual partner in the last 30 days. 87% (n=27) described heterosexual preference, whereas 13% (n=4) had homosexual preference. In describing level of sexual satisfaction on a scale of one to five, with five being most satisfied, 23% (n=7) described a maximum level of sexual satisfaction whereas 6.5% (n=2) described the lowest level of satisfaction with a median of three. As a means of assessing physiologic erectile function, frequency of morning erections was obtained. These were rated on a scale of one to five, one being absent and five being every morning. While 6% (n=2) described erections every morning, 3% (n=1) described the absence of morning erections, with a median of three. Most stated that odors never induced an erection (84%, or n=26), while 16% (n=5) admitted to odor-induced erection.

Results. The results are shown in Table 1 below. Sources of the odorants were Energy Essentials, IFF, AromaTech and essential oils.

The mixture of lavender and pumpkin pie odorants produced the greatest increase in median penile blood flow (40%). This was followed by the combination of black licorice and doughnut (31.5%), followed by pumpkin pie and doughnut (20%). The odor with the least effect on the median penile brachial index was cranberry which increased blood flow by 2%. Despite our hypothesis, no odor was found that reduced penile blood flow.

TABLE 1

| Odorant/Odorant Mixture | Median* |
| --- | --- |
| Lavender and pumpkin pie | 0.4000 |
| Doughnut and black licorice | 0.3150 |
| Pumpkin pie and doughnut | 0.2000 |
| Orange | 0.1950 |
| Lavender and doughnut | 0.1800 |
| Black licorice and cola | 0.1300 |
| Black licorice | 0.1300 |
| Doughnut and cola | 0.1250 |
| Lily of the valley | 0.1100 |
| Buttered popcorn | 0.0900 |
| Vanilla | 0.0900 |
| Pumpkin pie | 0.0850 |
| Lavender | 0.0800 |
| Musk | 0.0750 |
| Cola | 0.0700 |
| Doughnut | 0.0700 |
| Peppermint | 0.0600 |
| Cheese pizza | 0.0500 |
| Roasting meat | 0.0500 |
| Parsley | 0.0450 |

TABLE 1-continued

| Odorant/Odorant Mixture | Median* |
|---|---|
| Cinnamon buns | 0.0400 |
| Green apple | 0.0375 |
| Rose | 0.0350 |
| Strawberry | 0.0350 |
| Oriental spice | 0.0350 |
| Baby powder | 0.0325 |
| Floral | 0.0300 |
| Chocolate | 0.0275 |
| Pink grapefruit | 0.0250 |
| Cranberry | 0.0200 |

*Median penile blood flow

In those with normal olfactory ability, significant increase in brachial penile index correlated with (1) age and response to vanilla (p=0.05), (2) self assessed level of sexual satisfaction and response to strawberry (p=0.05), and (3) frequency of sexual intercourse and response to lavender (p=0.03), oriental spice (p=0.02) and cola (p=0.03).

Discussion. Although it was hypothesized that an odorant would be found that would reduce penile blood flow, no such odorant was identified. Such an odorant could be utilized to help decondition sex offenders. The results show that a hedonically positive odorant increased penile blood flow.

The present odors are not considered human pheromones which are believed to act upon the brain to cause an endocrinologic effect. Unlike pheromones, the present odorants that affected penile blood flow act immediately on the brain rather than in the slow manner of pheromones, or have an immediate psychological effect upon the brain.

There are several mechanisms by which the odorants may have affected penile blood flow. The odorants may have induced a Pavlovian conditioned response that reminded the subject of their sexual partners or their cooking and the associated mood states. Alternatively, odors may have induced a state of olfactory evoked recall. In a study of 989 people from 45 states and 39 countries, it was found that the odor that most induced olfactory evoked nostalgia response in those raised in the United States was that of baked goods (A. R. Hirsch, *Advances in Consumer Research* 19:390–395 (1992)). Although not wished to be held to any theory, odors that induced a nostalgic response and the associated positive mood state may have impacted upon penile blood flow. Or, the odors may have induced relaxation. Green apple has been suggested to reduce anxiety, and lavender, which increases alpha waves posteriorly, has been associated with a relaxed state (H. Sugano, *JASTS* XXII:8 (Abstract) (1988); J. R. King, "Anxiety reduction using fragrances," in *The Psychology and Biology of Fragrance*, pages 147–165, Van Toller and Dodd (eds.), Chapman and Hall, Ltd., London (1988)). Under a condition of reduced anxiety, inhibitions may have been removed and penile blood flow increased.

Alternatively, odors may have awakened the reticular activating system. Studies have indicated that jasmine increases beta waves frontally, and this is associated with a more alert state (Sugano (1988), supra). By making an individual more awake and alert, the odors may have caused subjects to be more aware of their entire environment, including any sexual cues around them, thus increasing penile blood flow.

Another possible mechanism is that the odorants may have acted neurophysically. It has been demonstrated that stimulation of the septal nucleus in the squirrel monkey induces erection (P. D. MacLean, "Cerebral evolution of emotion," in Lewis and Haviland (eds.), *Handbook of Emotions*, page 77, The Guilford Press, New York, N.Y. (1993)). A direct pathway connects the olfactory bulb to the septal nucleus (P. D. MacLean, *A Triune Concept of the Brain and Behavior*, page 14, University of Toronto Press, Toronto (1973)). Thus, it appears anatomically correct that odor may impact upon the septal nucleus and induce erection with associated increase in penile blood flow.

A direct physiologic mechanism may also play a role in the present method. One subject slept through the entire testing period, yet still showed the greatest increase in penile blood flow with the odors of the combination of lavender and pumpkin pie.

Alternatively, increased aggression through septal nucleus stimulation may be the primary effect. The increased penile blood flow may act not as a measure of direct sexual excitation, but may be the result of a "neighborhood effect" of induced aggression (Donatucci and Lue, "Physiology of Penile Tumescence," in *The Penis*, page 19, Hashmat and Das (eds.), Lea and Febiger, Philadelphia, Pa. (1993)).

In addition, a generalized parasympathetic effect, rather than specific sexual excitation, may act to increase penile blood flow. Primitive humans congregated around food kills, and there they had the greatest chance to procreate (J. Diamond, *The Third Chimpanzee: the evolution and future of the human animal*, page 68, Harper Collins Publisher, New York, N.Y. (1992). Thus, an increase in penile blood flow in response to food odors may have held a selective advantage for survival, and such a trait would be selected for through evolution.

Neuromechanisms for sexual excitation and penile erection. All natural functions are controlled by the nervous system, and the sexual response cycle is ultimately dependent on an intact neurophysiologic substrate. The sexual action can be viewed in the framework of Sherrington's reflex arc as a complicated knee jerk (W. Pryse-Phillips, *Companion to Clinical Neurology*, pages 785–786, Little, Brown and Company, Boston, Mass. (1995)).

There are several components that are involved. There is an afferent component of the sexual reflex arc which is activity by a diverse variety of exogenous stimuli: the primary stimulus consists of erotic visual, auditory, olfactory and tactile sensations. In addition, internal imagery, as well as REM periods of sleep, can serve as a primary stimulus of the sexual reflex. Each of these modes of activation act through different locations in the nervous system throughout the body. These stimuli are processed through specialized areas of the neocortex, limbic system and spinal cord, and then input into a final common pathway of sexual behavior. The efferent limb of the reflex arc involves a synchronized response of the voluntary and autonomic nervous system. Sexual stimulating odors rapidly traverse the afferent arc entering the limbic system and its neocortical connections.

There is also evidence that indicates that there is a direct connection between the olfactory bulb and the vomeronasal organ of the brain. In subhuman primates, the vomeronasal is where pheromones act (E. B. Keverne, "Pheromones and sexual behavior," in *Handbook of Sexology*, Money and Musaph (eds.), Elsevier/Horth-Holland Biomedical Press (1977)).

Thus, there are several pathways through which odors may impact upon sexual function. These pathways include: inducing memory through hippocampi connections, inducing direct penile effects through olfactory bulb septal nuclei connections, and/or affecting potential pheromonal action on the hypothalamus via the vomeronasal organ.

What is claimed is:

1. A method of increasing penile blood flow in a male individual, comprising:

administering to the male by inhalation of an odorant in an amount effective to increase penile blood flow;

the odorant selected from the group consisting of orange, a mixture of lavender and pumpkin pie a mixture of doughnut and black licorice, a mixture of pumpkin pie and doughnut lily of the valley, black licorice, a mixture of doughnut and cola, a mixture of black licorice and cola, a mixture of lavender and doughnut, chocolate, strawberry, rose, green, apple, parsley, peppermint, musk lavender, vanilla, cranberry, pink grapefruit, floral, baby powder, oriental spice, cinnamon buns, roasting meat, cheese pizza, doughnut, cola, pumpkin pie, and buttered popcorn.

2. A method of increasing penile blood flow in a male individual, comprising:

administering to the male by inhalation of an odorant in an amount effective to increase penile blood flow;

the odorant selected from the group consisting of a mixture of lavender and pumpkin pie, a mixture of doughnut and black licorice, and a mixture of pumpkin pie and doughnut.

3. A method of increasing penile blood flow in a mile individual, comprising:

administering to the male by inhalation of an odorant in an amount effective to increase penile blood flow;

wherein the odorant is selected from the group consisting of a doughnut odorant, a cinnamon buns odorant, a pumpkin pie odorant, a cola odorant, and an odorant mixture comprising one or more of those odorants.

4. An article of manufacture, comprising:

(a) an odorant as recited in claim 1 packaged within a container, wherein the odorant when inhaled by a male individual is effective to increase penile blood flow; and (b) instructions for use of the odorant according to the method of claim 1.

5. An article of manufacture, comprising:

(a) an odorant as recited in claim 2 packaged within a container, wherein the odorant when inhaled by a male individual is effective to increase penile blood flow in the male; and (b) instructions for use of the odorant according to the method of claim 2.

6. An article of manufacture, comprising:

(a) an odorant as recited in claim 3 packaged within a container, wherein the odorant when inhaled by a male individual is effective to increase penile blood flow; and (b) instructions for use of the odorant according to the method of claim 3.

7. The method of claim 1, wherein the odorant is administered in a form selected from the group consisting of a scented cloth, a liquid or solid form contained in a vessel having a cap, an aerosol spray, a pump-type spray, a nasal spray, a liquid or solid form contained in a blister pack, and microcapsules contained in a scratch-and-sniff odor patch.

8. The method of claim 1, wherein the odorant is administered in a form selected from the group consisting of a lotion, cream, perfume, and cologne.

9. The method of claim 1, wherein the odorant is administered by means of a pen-like dispenser containing the odorant in a liquid form.

10. The method of claim 2, wherein the odorant is administered in the form selected from the group consisting of a scented cloth, a liquid or solid form contained in a vessel having a cap, an aerosol spray, a pump-type spray, a nasal spray, a liquid or solid form contained in a blister pack, and microcapsules contained in a scratch-and-sniff odor patch.

11. The method of claim 2, wherein the odorant is administered in a form selected from the group consisting of a lotion, cream, perfume, and cologne.

12. The method of claim 2, wherein the odorant is administered by means of a pen-like dispenser containing the odorant in a liquid form.

13. The method of claim 3, wherein the odorant is administered in the form selected from the group consisting of a scented cloth, a liquid or solid form contained in a vessel having a cap, an aerosol spray, a pump-type spray, a nasal spray, a liquid or solid form contained in a blister pack, and microcapsules contained in a scratch-and-sniff odor patch.

14. The method of claim 3, wherein the odorant is administered in a form selected from the group consisting of a lotion, cream, perfume, and cologne.

15. The method of claim 3, wherein the odorant is administered by means of a pen-like dispenser containing the odorant in a liquid form.

16. A method of increasing penile blood flow in a male individual, comprising:

administering to the male by inhalation of an odorant in an amount effective to increase penile blood flow;

the odorant administered in a form selected from the group consisting of a scented cloth, a liquid or solid form contained in a vessel having a cap, an aerosol spray, a pump-type spray, a nasal spray, a liquid or solid form contained in a blister pack, and microcapsules contained in a scratch-and-sniff odor patch; and the odorant selected from the group consisting of orange, a mixture of lavender and pumpkin pie, a mixture of doughnut and black licorice, a mixture of pumpkin pie and doughnut, lily of the valley, black licorice, a mixture of doughnut and cola, a mixture of black licorice and cola, a mixture of lavender and doughnut, chocolate, strawberry, rose, green apple, parsley, peppermint, musk, lavender, vanilla, cranberry, pink grapefruit, floral, baby powder, oriental spice, cinnamon buns, roasting meat, cheese pizza, doughnut, cola, pumpkin pie, and buttered popcorn.

17. The method of claim 16, wherein the odorant is administered in a form selected from the group consisting of a lotion, cream, perfume, and cologne.

18. The method of claim 16, wherein the odorant is administered by means of a pen-like dispenser containing the odorant in a liquid form.

19. A method of increasing penile blood flow in a male individual, comprising:

administering to the male by inhalation of an odorant in an amount effective to increase penile blood flow;

the odorant administered in a form selected from the group consisting of a scented cloth, a liquid or solid form contained in a vessel having a cap, an aerosol spray, a pump-type spray, a nasal spray, a liquid or solid form contained in a blister pack, and microcapsules contained in a scratch-and-sniff odor patch;

the odorant selected from the group consisting of orange, a mixture of lavender and pumpkin pie, a mixture of doughnut and black licorice, a mixture of pumpkin pie and doughnut, lily of the valley, black licorice, a mixture of doughnut and cola, a mixture of black licorice and cola, and a mixture of lavender and doughnut.

20. The method of claim 19, wherein the odorant is administered in a form selected from the group consisting of a lotion, cream, perfume, and cologne.

21. The method of claim 19, wherein the odorant is administered by means of a pen-like dispenser containing the odorant in a liquid form.

22. An article of manufacture, comprising:
(a) an odorant as recited in claim 16 and packaged in a recited form, wherein the odorant when inhaled by a male individual is effective to increase penile blood flow; and
(b) instructions for use of the odorant according to the method of claim 16.

23. An article of manufacture, comprising:
(a) an odorant as recited in claim 19 and packaged in a recited form, wherein the odorant when inhaled by a male individual is effective to increase penile blood flow; and
(b) instructions for use of the odorant according to the method of claim 19.

* * * * *

UNITED STATES PATENT AND TRADEMARK OFFICE
CERTIFICATE OF CORRECTION

PATENT NO. : 5,885,614
DATED : MARCH 23, 1999
INVENTOR(S) : Alan R. Hirsch

It is certified that error appears in the above-identified patent and that said Letters Patent is hereby corrected as shown below:

At cols. 8-9, claim 1 should read as

--A method of increasing penile blood flow in a male individual, comprising:

administering to the male by inhalation of an odorant in an amount effective to increase penile blood flow;

the odorant selected from the group consisting of orange, a mixture of lavender and pumpkin pie, a mixture of doughnut and black licorice, a mixture of pumpkin pie and doughnut, lily of the valley, black licorice, a mixture of doughnut and cola, a mixture of black licorice and cola, a mixture of lavender and doughnut, chocolate, strawberry, rose, green apple, parsley, peppermint, musk, lavender, vanilla, cranberry, pink grapefruit, floral, baby powder, oriental spice, cinnamon buns, roasting meat, cheese pizza, doughnut, cola, pumpkin pie, and buttered popcorn.--

Signed and Sealed this

Seventeenth Day of August, 1999

Attest:

Q. TODD DICKINSON

*Attesting Officer*                *Acting Commissioner of Patents and Trademarks*